United States Patent
Hendriks et al.

(10) Patent No.: US 8,771,176 B2
(45) Date of Patent: Jul. 8, 2014

(54) CAPSULE CAMERA WITH VARIABLE ILLUMINATION OF THE SURROUNDING TISSUE

(75) Inventors: Bernardus Hendrikus Wilhelmus Hendriks, Eindhoven (NL); Michael Harald Kuhn, Hamburg (DE); Thomas Zaengel, Aachen (DE); Nijs Cornelis Van Der Vaart, Rosmalen (NL)

(73) Assignee: Koninklijke Philips N.V., Eindhoven (NL)

(*) Notice: Subject to any disclaimer, the term of this patent is extended or adjusted under 35 U.S.C. 154(b) by 701 days.

(21) Appl. No.: 12/374,506

(22) PCT Filed: Apr. 12, 2007

(86) PCT No.: PCT/IB2007/051323
§ 371 (c)(1),
(2), (4) Date: Jan. 21, 2009

(87) PCT Pub. No.: WO2008/012701
PCT Pub. Date: Jan. 31, 2008

(65) Prior Publication Data
US 2009/0177033 A1 Jul. 9, 2009

Related U.S. Application Data

(60) Provisional application No. 60/820,124, filed on Jul. 24, 2006.

(51) Int. Cl.
*A61B 1/06* (2006.01)
(52) U.S. Cl.
USPC ............ 600/167; 600/173; 600/177; 600/178
(58) Field of Classification Search
USPC .................. 600/109, 160, 167, 173, 177, 178; 359/665, 666
See application file for complete search history.

(56) References Cited

U.S. PATENT DOCUMENTS

| | | | | |
|---|---|---|---|---|
| 4,951,663 A | * | 8/1990 | L'Esperance, Jr. | 607/89 |
| 5,098,426 A | * | 3/1992 | Sklar et al. | 606/5 |

(Continued)

FOREIGN PATENT DOCUMENTS

| | | |
|---|---|---|
| WO | 0236007 A1 | 5/2002 |
| WO | 02058531 A2 | 8/2002 |

(Continued)

OTHER PUBLICATIONS

Dolmans et al., "Photodynamic therapy for cancer", Nature Reviews Cancer 2003, pp. 380-387, vol. 3.

(Continued)

*Primary Examiner* — Philip R Smith
*Assistant Examiner* — William Chou

(57) ABSTRACT

The application relates to an ingestible capsule and method for in vivo imaging and/or treatment of one or more diseased areas of interest within the gastrointestinal tract of an animal or human being. The capsule comprises an image sensor; a lens system for focusing images onto the image sensor; at least one light source for illumination of the tissue area of interest, the at least one light source optionally being capable of providing optical therapeutic treatment to the diseased areas; a variable lens system located in front of the at least one light source, wherein the variable lens system comprises beam steering means and focusing means for directing and focusing the light beams from the at least one light source onto the diseased tissue areas, —a control unit in communication with the image sensor, the at least one light source, and variable lens system, a power source for powering the image sensor, the at least one light source and the control unit; and a non-digestible, transparent outer protective shell configured to pass through the gastrointestinal tract, housing within the image sensor, the lens system, the at least one light source, the variable lens system, the control unit and the power source.

10 Claims, 3 Drawing Sheets

(56) References Cited

U.S. PATENT DOCUMENTS

| | | | |
|---|---|---|---|
| 5,604,531 A | 2/1997 | Iddan et al. | |
| 6,240,312 B1 | 5/2001 | Alfano et al. | |
| 6,855,111 B2 | 2/2005 | Yokoi et al. | |
| 6,950,690 B1 | 9/2005 | Meron et al. | |
| 7,022,067 B2 * | 4/2006 | Glukhovsky et al. | 600/109 |
| 7,044,908 B1 | 5/2006 | Montalbo et al. | |
| 7,530,948 B2 * | 5/2009 | Seibel et al. | 600/178 |
| 2001/0051766 A1 * | 12/2001 | Gazdzinski | 600/309 |
| 2002/0006264 A1 * | 1/2002 | Birk et al. | 385/147 |
| 2003/0208107 A1 * | 11/2003 | Refael | 600/300 |
| 2004/0061072 A1 * | 4/2004 | Gu et al. | 250/458.1 |
| 2004/0254474 A1 * | 12/2004 | Seibel et al. | 600/473 |
| 2005/0002945 A1 | 1/2005 | McBride et al. | |
| 2005/0043586 A1 | 2/2005 | Suzushima | |
| 2005/0096712 A1 * | 5/2005 | Abraham-Fuchs et al. | 607/89 |
| 2005/0137468 A1 | 6/2005 | Avron et al. | |
| 2005/0215911 A1 * | 9/2005 | Alfano et al. | 600/476 |
| 2006/0082648 A1 | 4/2006 | Iddan et al. | |
| 2006/0100486 A1 | 5/2006 | Maschke | |
| 2006/0195014 A1 * | 8/2006 | Seibel et al. | 600/102 |
| 2006/0195015 A1 * | 8/2006 | Mullick et al. | 600/102 |
| 2007/0066871 A1 * | 3/2007 | Yang et al. | 600/173 |
| 2008/0103355 A1 * | 5/2008 | Boyden et al. | 600/103 |
| 2009/0281389 A1 * | 11/2009 | Iddan | 600/167 |

FOREIGN PATENT DOCUMENTS

| | | |
|---|---|---|
| WO | 2004051323 A1 | 6/2004 |
| WO | 2006070356 A2 | 7/2006 |

OTHER PUBLICATIONS

Gibson et al., "Recent advances in diffuse optical imaging", Phys. Med. Biol., 2005, R1-R43, vol. 50.

Herz, P.R. et al. "Micromotor Endoscope Catheter for Invivo, Ultrahigh-Resolution Optical Coherence Tomography", OPTICS Letters, vol. 29, No. 19, Oct. 2004, pp. 2261-2263.

* cited by examiner

CAPSULE CAMERA WITH VARIABLE ILLUMINATION OF THE SURROUNDING TISSUE

The present disclosure is directed to an ingestible capsule and a method for in vivo imaging and/or treatment of one or more diseased areas of interest within the gastrointestinal tract of an animal or human being using such ingestible capsule.

Ingestible capsules or medical devices for imaging the gastrointestinal tract of mammals (animals or human beings) have been disclosed in the prior art, such as, in U.S. Pat. Nos. 5,604,531; 6,855,111; and 6,950,690; U.S. Patent Applications 2006/0082648 (published Apr. 20, 2006); 2005/0137468 (published Jun. 23, 2005); 2005/0002945 (published Jan. 6, 2005); and 2006/0100486 (published May 11, 2006); and PCT Publications WO 2004/051323 (published Jun. 17, 2004); WO 2002/306007 (published May 10, 2002); and WO 2002/058531 (published Aug. 1, 2002).

Typically, a capsule camera is adapted for in vivo imaging within a patient's body after ingestion thereof, taking image scenes of, for example, the gastro-intestinal tract. A conventional capsule camera (see FIG. 1) has a waterproof, transparent outer housing 30, of dimensions less than 5 cm by 3 cm, such that capsule may be readily indigested by the patient. A lens system 32 is located inside the capsule housing 30 in front of an imaging sensor 34, for example a Charge Coupled Device (CCD) or Complementary Metal-Oxide Semiconductor (CMOS) image sensor, to provide an imaging scene onto the sensor. Lens 32 may be a single or multi element lens system and may include focusing and/or zoom functionality. Two light sources 36, 38 (e.g., lasers or light emitting diodes (LEDs)), are located adjacent the lens 32 to project light onto the surrounding imaging region. The capsule further typically includes a control unit 40, which includes image storage memory and/or image transmission apparatus, such as a microwave transmitter, which transmits images to an external pickup device. A power source 42, such as a battery or a magnetic coil set, is also generally provided. Power source 42 can be externally driven with a magnetic signal to produce electrical power. This capsule camera module is therefore able to provide continuous imaging functionality in a compact, low power consumption and lightweight module.

In WO 2004/051323, a variable lens system is described that is placed in front of the sensor, thereby allowing variable focus/zooming and/or variable directed imaging function in a compact, low power consumption and lightweight module. Only imaging functionality is addressed in this publication, allowing in some cases diagnoses of diseases of the gastrointestinal tract. Further inspection or the treatment of these diseases with light is not addressed. In order to allow optical treatment with light, the area to be treated must be identified and, once the treatment area has been identified, the light beam must be focused on this area and kept in focus for some time while the capsule moves along.

Another problem arises when a certain area of interest is to be further inspected with optical methods requiring a focused light beam to be aimed at the area-of-interest while the capsule moves along. With the noted prior art devices, focused inspection is not possible because the light beam is a broad field illumination beam.

Despite efforts to date, a need remains for ingestible devices and/or an ingestible systems that facilitate effective focus of a light beam on a desired in vivo location, e.g., an identified lesion, either for treatment or for further inspection. In addition, a need remains for an apparatus and/or system that facilitates in vivo light focus and/or beam steering in connection with a capsule camera.

These and other needs are satisfied with the devices, systems and methods of the present disclosure.

According to the present disclosure, an ingestible capsule and method for in vivo imaging and/or treatment of diseased tissue in the gastrointestinal tract of an animal or human being is disclosed. The capsule comprises an image sensor; a lens system for focusing images onto the image sensor; at least one light source, and preferably first and second light sources, for illumination of the tissue area of interest, the second light source optionally being capable of providing optical therapeutic treatment to the diseased areas; a variable lens system located in front of the first light source, wherein the variable lens system comprises beam steering means and focusing means for directing and focusing the light beams from the first light source onto the diseased tissue areas; a control unit in communication with the image sensor, first and second light sources, and variable lens system, the control unit comprising image storing means, processing means and image transmission means; wherein the control unit correlates stored images received from the image sensor as the capsule travels through the gastrointestinal tract and controls the beam steering means and focusing means of the variable lens system to ensure that the light beams from the first light source are directed and focused onto the diseased tissue areas; a power source for powering the image sensor, the first and second light sources and the control unit; and a non-digestible, transparent outer protective shell configured to pass through the gastrointestinal tract, housing within the image sensor, the lens system, the first and second light sources, the variable lens system, the control unit and the power source.

Specifically it is an object of the invention to provide an ingestible capsule for in vivo imaging and/or treatment of one or more diseased tissue areas of interest within the gastrointestinal tract of an animal or human being, said capsule comprising:

an image sensor;
a lens system for focusing images of interest onto the image sensor;
at least one light source for providing illumination to the tissue of the gastrointestinal tract; wherein the at least one light source is optionally capable of providing optical therapeutic treatment to the diseased tissue areas;
a variable lens system located in front of the at least one light source, wherein the variable lens system comprises beam steering means and focusing means for directing and focusing the light beams from the at least one light source onto the diseased tissue areas;
a control unit in communication with the image sensor, the at least one light source, and variable lens system, the control unit comprising image storing means, processing means and image transmission means; wherein the control unit correlates stored images received from the image sensor as the capsule travels through the gastrointestinal tract and controls the beam steering means and focusing means of the variable lens system to ensure that the light beams from the at least one light source are directed and focused onto the diseased tissue areas;
a power source for powering the image sensor, the at least one light source and the control unit; and
a non-digestible, transparent outer protective shell configured to pass through the gastrointestinal tract, housing within the image sensor, the lens system, the at least one light source, the variable lens system, the control unit and the power source.

Another object is to provide an ingestible capsule for in vivo imaging and/or treatment of one or more diseased tissue areas of interest within the gastrointestinal tract of an animal or human being, said capsule comprising:

an image sensor;

a lens system for focusing images of interest onto the image sensor;

first and second light sources for providing illumination to the tissue of the gastrointestinal tract; wherein the second light source is optionally capable of providing optical therapeutic treatment to the diseased tissue areas;

a variable lens system located in front of the first light source, wherein the variable lens system comprises beam steering means and focusing means for directing and focusing the light beams from the first light source onto the diseased tissue areas;

a control unit in communication with the image sensor, first and second light sources, and variable lens system, the control unit comprising image storing means, processing means and image transmission means; wherein the control unit correlates stored images received from the image sensor as the capsule travels through the gastrointestinal tract and controls the beam steering means and focusing means of the variable lens system to ensure that the light beams from the first light source are directed and focused onto the diseased tissue areas;

a power source for powering the image sensor, the first and second light sources and the control unit; and a non-digestible, transparent outer protective shell configured to pass through the gastrointestinal tract, housing within the image sensor, the lens system, the first and second light sources, the variable lens system, the control unit and the power source.

Another object is to provide a capsule wherein the first and second light sources are each lasers.

Another object is to provide a capsule wherein the variable lens system comprises a liquid lens system.

Another object is to provide a method for in vivo imaging of one or more tissue areas of interest within the gastrointestinal tract of an animal or human being comprising: ingesting a capsule comprising:

an image sensor;

a lens system for focusing images of interest onto the image sensor;

at least one light source for providing illumination to the tissue of the gastrointestinal tract; wherein the at least one light source is optionally capable of providing optical therapeutic treatment to the diseased tissue areas;

a variable lens system located in front of the at least one light source, wherein the variable lens system comprises beam steering means and focusing means for directing and focusing the light beams from the at least one light source onto the diseased tissue areas;

a control unit in communication with the image sensor, the at least one light source, and variable lens system, the control unit comprising image storing means, processing means and image transmission means; wherein the control unit correlates stored images received from the image sensor as the capsule travels through the gastrointestinal tract and controls the beam steering means and focusing means of the variable lens system to ensure that the light beams from the at least one light source are directed and focused onto the diseased tissue areas;

a power source for powering the image sensor, the at least one light source and the control unit; and a non-digestible, transparent outer protective shell configured to pass through the gastrointestinal tract, housing within the image sensor, the lens system, the at least one light source, the variable lens system, the control unit and the power source;

transmitting the image data from the control unit to an external image receiving and viewing unit, and viewing the image data.

Another object is to provide a method for in vivo imaging of one or more tissue areas of interest within the gastrointestinal tract of an animal or human being comprising: ingesting a capsule comprising:

an image sensor;

a lens system for focusing images of interest onto the image sensor;

first and second light sources for providing illumination to the tissue of the gastrointestinal tract; wherein the second light source is optionally capable of providing optical therapeutic treatment to the diseased tissue areas;

a variable lens system located in front of the first light source, wherein the variable lens system comprises beam steering means and focusing means for directing and focusing the light beams from the first light source onto the diseased tissue areas;

a control unit in communication with the image sensor, first and second light sources, and variable lens system, the control unit comprising image storing means, processing means and image transmission means; wherein the control unit correlates stored images received from the image sensor as the capsule travels through the gastrointestinal tract and controls the beam steering means and focusing means of the variable lens system to ensure that the light beams from the first light source are directed and focused onto the diseased tissue areas;

a power source for powering the image sensor, the first and second light sources and the control unit; and a non-digestible, transparent outer protective shell configured to pass through the gastrointestinal tract, housing within the image sensor, the lens system, the first and second light sources, the variable lens system, the control unit and the power source;

transmitting the image data from the control unit to an external image receiving and viewing unit, and viewing the image data.

Another object is to provide a method for in vivo treatment of one or more diseased tissue areas of interest within the gastrointestinal tract of an animal or human being comprising:

ingesting into the gastrointestinal tract a fluorescence marking agent that will chemically bind to the diseased tissue areas only and cause the diseased tissue areas to transmit fluorescent light beams when stimulated by a light source;

thereafter ingesting a capsule comprising:

an image sensor;

a lens system for focusing images of interest onto the image sensor;

at least one light source for providing illumination to the tissue of the gastrointestinal tract; wherein the at least one light source is a laser capable of providing optical therapeutic treatment to the diseased tissue areas;

a variable lens system located in front of the at least one light source, wherein the variable lens system comprises beam steering means and focusing means for directing and focusing the light beams from the at least one light source onto the diseased tissue areas;

a control unit in communication with the image sensor, at least one light source, and variable lens system, the control unit comprising image storing means, processing means and image transmission means; wherein the control unit correlates stored images received from the image sensor as the capsule travels through the gastrointestinal tract and controls the beam steering means and focusing means of the variable lens system to ensure that the light beams from the at least one light source are directed and focused onto the diseased tissue areas;

a power source for powering the image sensor, the at least one light source and the control unit; and a non-digestible, transparent outer protective shell configured to pass through the gastrointestinal tract, housing within the image sensor, the lens system, the at least one light source, the variable lens system, the control unit and the power source:

causing the at least one light source to illuminate and excite the diseased tissue areas having bound fluorescent agent to transmit fluorescent light images to the lens system, image sensor and control unit; wherein the control unit controls the variable lens focusing means and beam steering means to ensure illumination of the diseased areas by the at least one light source; and causing the at least one light source to optically treat the diseased areas.

Another object is to provide a method for in vivo treatment of one or more diseased tissue areas of interest within the gastrointestinal tract of an animal or human being comprising:

ingesting into the gastrointestinal tract a fluorescence marking agent that will chemically bind to the diseased tissue areas only and cause the diseased tissue areas to transmit fluorescent light beams when stimulated by a light source;

thereafter ingesting a capsule comprising:

an image sensor;

a lens system for focusing images of interest onto the image sensor;

first and second light sources for providing illumination to the tissue of the gastrointestinal tract; wherein the second light source is a laser capable of providing optical therapeutic treatment to the diseased tissue areas;

a variable lens system located in front of the first light source, wherein the variable lens system comprises beam steering means and focusing means for directing and focusing the light beams from the first light source onto the diseased tissue areas;

a control unit in communication with the image sensor, first and second light sources, and variable lens system, the control unit comprising image storing means, processing means and image transmission means; wherein the control unit correlates stored images received from the image sensor as the capsule travels through the gastrointestinal tract and controls the beam steering means and focusing means of the variable lens system to ensure that the light beams from the first light source are directed and focused onto the diseased tissue areas;

a power source for powering the image sensor, the first and second light sources and the control unit; and a non-digestible, transparent outer protective shell configured to pass through the gastrointestinal tract, housing within the image sensor, the lens system, the first and second light sources, the variable lens system, the control unit and the power source:

causing the first light source to illuminate and excite the diseased tissue areas having bound fluorescent agent to transmit fluorescent light images to the lens system, image sensor and control unit; wherein the control unit controls the variable lens focusing means and beam steering means to ensure illumination of the diseased areas by the first light source; and causing the second light source to optically treat the diseased areas.

Another object is to provide a method wherein the first and second light sources are each lasers.

Another object is to provide a method wherein the variable lens system comprises a liquid lens system.

Another object is to provide a method wherein the treatment comprises thermo-ablation of a lesion or tumor; or coagulation of a bleeding blood vessel or bleeding tumor.

These and other aspects of the invention are explained in more detail with reference to the following embodiments and with reference to the figures.

Figure 1:
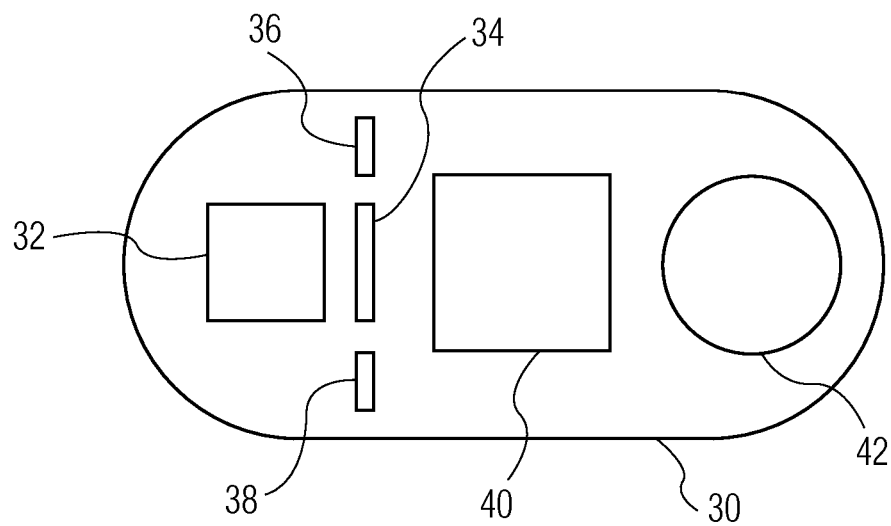
FIG. 1 is a conceptual representation of a conventional capsule camera.

To overcome the problems associated with prior disclosed medical devices and ingestible capsules, the herein disclosed ingestible capsule and method utilize a variable lens placed in front of the light source, for instance a liquid lens. The liquid lens has been discussed in detail in WO2003/069381. In order to allow beam steering, also additional electrodes have to be used on the exterior of the liquid lens described in WO2004/051323, which is incorporated by reference herein in its entirety. Although making use of a liquid enabling focusing and beam steering of the light beam, it still does not solve the problem of how to keep the focus spot on the tissue area to be treated or further inspected. To solve this problem we make use of the camera system, including 32 and 34, in combination with the illumination device 38. When 38 is switched on, the camera takes an image, from which the area of interest can be identified by the image processing unit 40 (see FIG. 2). Shortly after this image has been taken, the first source 38 is switched off and the second light source 36 used for treatment or further diagnostics is turned on at a low intensity light level. Although the light sources 38 and 36 are described here as separate light sources they may also be one single light source with multiple functionality (e.g., for illumination, for treatment, etc.). Also, there may be more than two light sources, for example three, four or more. The image of this spot on the camera sensor using source 36, and that of the area of interest from the first image using source 38, can be correlated. An additional application is that two images taken from the camera, while the capsule has moved, can also be used for stereophotogrammetric calculation of depth information. This has been disclosed and used for endoscopes, but not for capsule cameras. If the areas do not overlap, adjustment of the liquid lens follows and the procedure is repeated. If correlation is reached, the intensity of beam 36 is switched to the level allowing treatment or further investigation.

In case of treatment, the requirement on diagnosing the right tissue area with the camera is important. To improve this step, fluorescence markers can be used. In this case the light source 38 is used also to illuminate the lesion to induce fluorescence by the targeted marker. Apart from fluorescence this can be generalized to include also autofluorescence/bioluminescence. By correlating the treatment spot with the fluorescence spot in the way described above, this modality can be used for aiming at the treatment spot. The fluorescence will also give an indication where ablation or other treatment has to be performed. Without it, the camera image needs to be analyzed in order to find the pathology. It is also possible to use multiple fluorescent labels which emit at different wavelengths and can thus provide information on different proteins in the lesion, which may require different treatments.

Exemplary Applications According to the Invention

Examples of Treatment.

When the treatment light source is a laser, a thermal effect on the lesion or tumor can be employed for thermo-ablation of the lesion or tumor. The thermal effect of the laser can also be used for coagulation of a bleeding vessel or the bleeding surface of a tumor.

Another example is that the light source is used as a source of non-thermal light for photodynamic therapy (PDT) (see for instance DEJC Dolmans, D Fukumura and RK Jain, "Photodynamic therapy for cancer", in Nature Reviews Cancer 2003 vol. 3 page 380-387). This requires the use of photosensitiser agents. It is also possible that a photosentizing agent is locally released by the capsule when it detects a suspicious lesion (or on a continuous basis, which requires a larger reservoir).

Example of Further Investigation.

Confocal Microscopy

Figure 2:
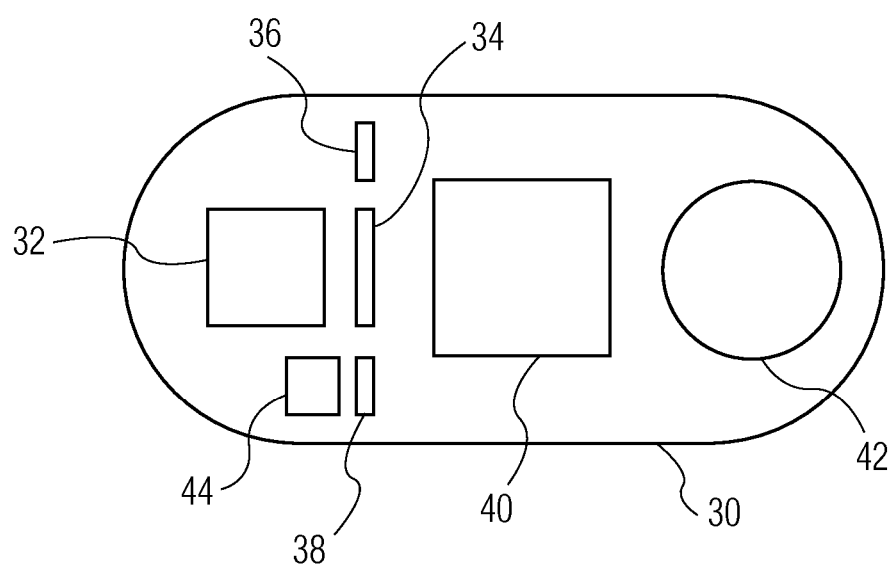
FIG. 2 is a conceptual representation of the capsule camera according to the invention.
Figure 3:
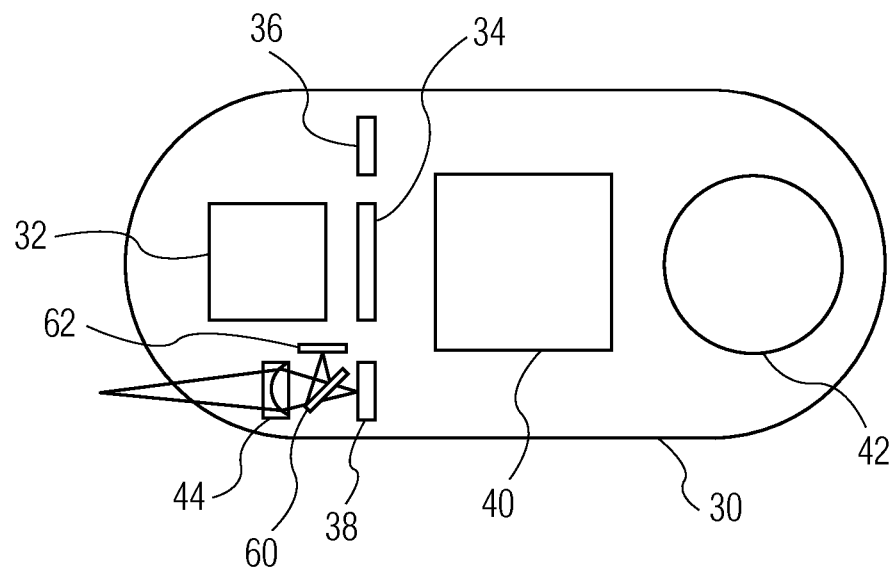
FIG. 3 is a conceptual representation of the capsule camera with confocal microscopy imaging according to the invention.

An example of an application according to the invention is employing confocal microscopy (see FIGS. 2 and 3). In this case, the light source is a point source that is focused somewhere in the tissue. The set-up is such that the focal plane of the confocal microscope is such that this plane is imaged in focus on the image sensor 34 of the camera 34 and 32.

In case of a confocal scanning microscope the light beam, produced by a laser 38, passes a partial beam splitter 60 and is aimed and focused by the liquid lens 44 on the lesion of interest. The reflected signal following the same return path is now focused by the liquid lens 44 via reflection on the partial beam splitter 60 onto the detector 62 via a pinhole or aperture present in front of the detector. By scanning the beam by changing the setting of the variable lens 44 an image with the confocal microscope of the lesion can be taken. In order to do proper image reconstruction, motion of the capsule has to be corrected for. This can be accomplished by using the capsule camera according to the invention.

Fluorescence Imaging

In case of fluorescence imaging process, the laser beam is brought in focus with the lesion or tumor. The fluorescence induced by the light absorption is detected by a detector module.

We can use for instance the same set-up as described for the confocal microscope. Since now we are looking for fluorescence produced by light absorption we adapt the detector in order to record the fluorescence light spectrally resolved.

Diffuse Optical Tomography (DOT)

Figure 4:
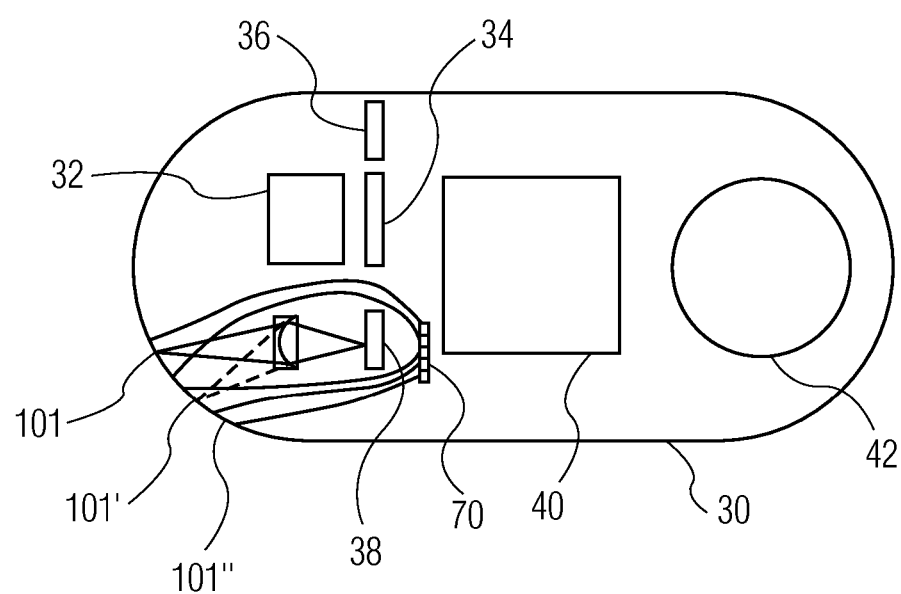
FIG. 4 is a conceptual representation of the capsule camera with diffuse optical imaging functionality according to the invention.

In this case the light source consist of one or more light emitters that enable subsequent point like illumination of the adjacent tissue around the capsule that at least contains positions that are transparent for the light (see FIG. 4). When for instance site 101 is illuminated by the source 38, light will diffusely scatter through the tissue and reach for instance detector fibers connected to the detector 70. The signal of all the detection fibers are collected and stored in a memory. This measurement is repeated for each illumination site 101', 101", etc. All the measurements are now used to perform an image reconstruction (see for instance A P Gibson, J C Hebden and S R Arridge, "Recent advances in diffuse optical imaging" in Phys. Med. Biol. Vol. 50 (2005) R1-R43). In order to compensate for the movement of the sample, the images on the camera 34, 32 can be used.

Optical Coherence Tomography (OCT)

Figure 5:
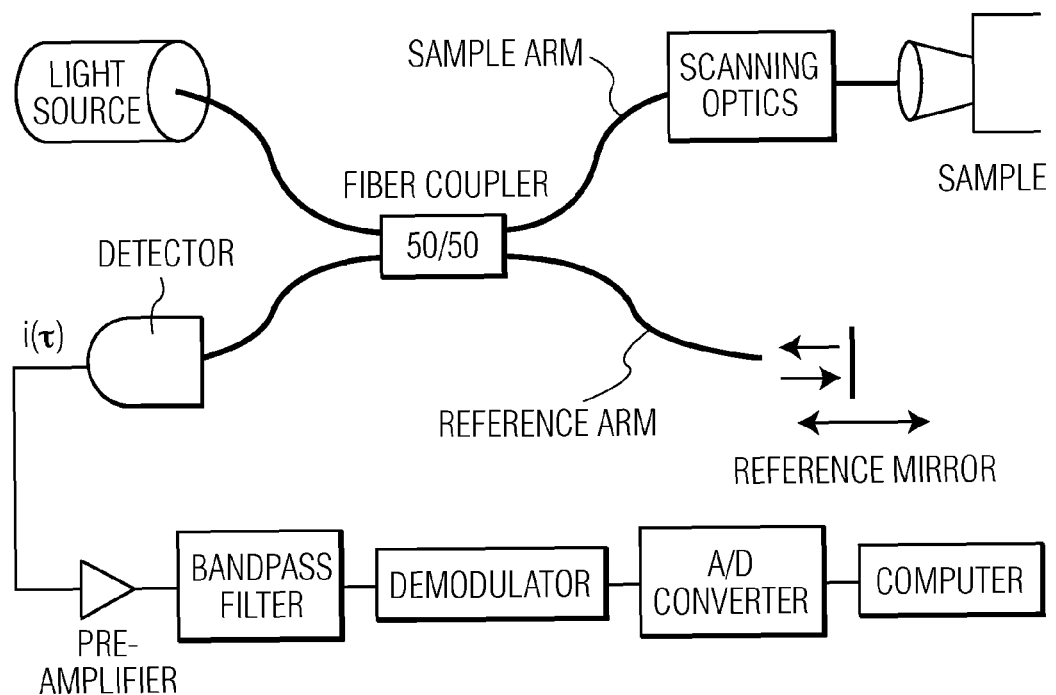
FIG. 5 is a conceptual representation of a basic fiber based Optical Coherence Tomography (OCT) schematic.

OCT is an imaging technology that achieves up to a few millimeters penetration depth (1.5-2 mm typically) at ultra-high resolution (several microns) generating 3D tissue images in real time. OCT provides 3D structural image (tissue layers, density changes), showing currently great potential to provide spectroscopic information and to achieve functional and molecular imaging as well. OCT is an interferometry-based technology, capable of measuring signals as small as −90 dB. One standard fiber based OCT set-up is shown in FIG. 5.

Light coming from a light source is split by a coupler. One arm serves as a sample (reference) arm of the interferometer, while the other one delivers light to the sample (sample arm). The scanning optics provides lateral scanning capabilities, so that the OCT set-up obtains one A-scan (axial-scan) for each lateral position. All A-scans combined form a 3D structural image. When obtaining each A-scan the reference mirror's displacement provides depth information. Several more advanced techniques have been developed to achieve depth information in shorter times than the one shown here. Spectroscopic OCT is the most advanced among those, providing depth scans data with no moving parts. Currently the fastest OCT systems can produce images on around 30 fps, with more than 1000 A-scans per frame. Lateral resolution is limited by the scanning optics and light focusing system. Axial resolution is light source dependent. A typical axial resolution currently accessible with commercial SLDs (super luminescence diodes, bandwidth around 70 nm at 930 nm) is approximately 5 µm. One of the best demonstrated resolutions of around 1.5 µm was achieved by using a Ti:sapphire fs laser.

To make this suitable for use in the capsule according to the invention the system has to be miniaturised. From the engine side OCT requires:

i) Light source. It determines axial resolution, which is proportional to the source bandwidth. Commercially available SLDs (super luminescence diodes) obtain around 5 µm axial resolution. Better resolution is available if Ti:Sapphire fs laser or Tungsten lamp (very low power) is used (resolution close to 1 µm). Tunable laser is needed for Fourier domain OCT.

ii) Fiber optics components. Fibers to provide light delivery, fiber coupler and/or circulator to realize Michelson interferometer.

iii) Detection components. Dependent on OCT type. Photodiodes typically, but in the case of spectral OCT spectrally resolved detection is needed (spectrum analyzer in combination with a liner CCD array).

iv) In case of polarization or phase OCT the engine and the probe components have to be able to maintain light polarization properties.

Figure 6:
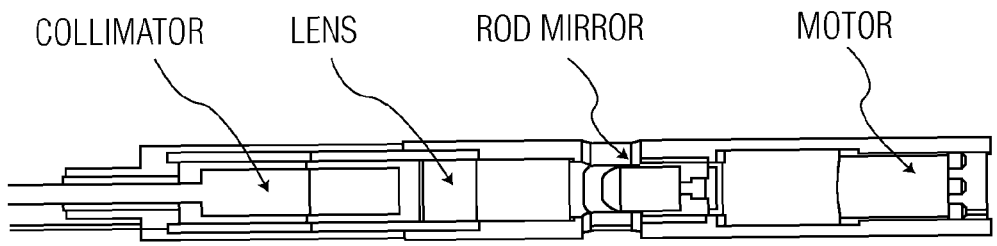
FIG. 6 is a schematic of a miniaturized catheter type of probe (about 2 mm diameter)( from Optics Letters 29, 2261 (2004)) based on a fiber optics type of device combining an optical delivery system (fiber) with a simple focusing mechanism (GRIN lens type).

Although at the moment no such miniaturised device exist it is envisaged that in the near future miniaturisation allows the construction of such a device. For instance, a miniaturised probe design has been described in Optics Letters 29, 2261 (2004) (see FIG. 6).

While the present invention has been described with respect to specific embodiments thereof, it will be recognized by those of ordinary skill in the art that many modifications, enhancements, and/or changes can be achieved without departing from the spirit and scope of the invention. Therefore, it is manifestly intended that the invention be limited only by the scope of the claims and equivalents thereof.

The invention claimed is:

1. An ingestible untethered capsule for in vivo imaging and/or treatment of diseased tissue within a gastrointestinal tract of an animal or human being, said capsule comprising:
   a camera including an image sensor and a first lens located in front of the image sensor for taking images of the diseased tissue;
   at least one light source located laterally adjacent the image sensor for providing one or more light beams for illumination and optical therapeutic treatment of the diseased tissue;
   a second lens located in front of the at least one light source for focusing at least one of the light beams from the at least one light source on a focus spot along a first path in a first direction onto the diseased tissue; and
   a controller connected to the camera and the second lens and configured to correct for motion of the capsule by controlling the second lens to maintain the focus spot as the capsule moves within the gastrointestinal tract.

2. The ingestible capsule of claim 1, wherein the at least one light source includes first and second light source, the second light source providing optical therapeutic treatment to the diseased tissue.

3. The capsule of claim 2, wherein the first and second light sources comprise lasers.

4. The capsule of claim 1, wherein the second lens comprises a liquid lens system.

5. The capsule of claim 1, further comprising an outer protective shell, wherein the outer protective shell is non-digestible, transparent, and configured to pass through the gastrointestinal tract.

6. The capsule of claim 1, further comprising a power source for powering the image sensor, the at least one light source and the control unit.

7. The capsule of claim 1, wherein the controller further comprising a memory for storing images received from the image sensor as the capsule travels through the gastrointestinal tract and a transmitter for transfer the stored images, the controller is configured to control the at least one light source and the second lens and to correlate and transfer the stored images.

8. The capsule of claim 1, wherein the power source is externally driven with a magnetic signal to produce electrical power to enable continuous imaging and treatment of the diseased tissue.

9. The capsule of claim 1, further comprising
   a detector located in front of the at least one light source configured to detect second light beams reflected from the diseased tissue in a second direction opposite the first direction along the first path; and
   a beam splitter configured to focus the light beams and the reflected second light beams on the detector through an aperture,
   wherein to correct for motion of the capsule the controller correlates successive images of the focus spot and keeps the focus spot on the tissue area to be treated by changing settings of the second lens that is scanning the reflected light beams.

10. An ingestible untethered capsule for in vivo imaging and/or treatment diseased tissue within a gastrointestinal tract of animal or human being, said capsule comprising:
    a camera including an image senor and first lens located in front of the image sensor for taking in images of the diseased tissue;
    at least one light source located laterally adjacent the camera for providing one or more light beams for illumination and optical therapeutic treatment of the diseased tissue;
    a second lens located in front of the at least one light source for focusing at least one of the light beams from the at least one light source on a focus spot along a first path in a first direction onto the diseased tissue; and
    a detector located in front of the at least one light source for detecting second light beams reflected from the diseased tissue in a second direction opposite the first direction along the first path;
    a beam splitter located in front of the detector and configured to focus the light beams and the reflected second light beams on the detector through an aperture; and
    a controller connected to the camera, the second lens, and the beam splitter and configured to correct for motion of the capsule by changing settings of the second lens to maintain the focus spot, after reconstructing the images of the diseased tissue,
    wherein the second lens is scanning the reflected light beams.

* * * * *